United States Patent

Jentges

[11] Patent Number: 4,579,124
[45] Date of Patent: Apr. 1, 1986

[54] AIR FLOW MEASURING INSTRUMENT FOR SPEECH THERAPY

[76] Inventor: Helen C. Jentges, W. 2211 Holyoke, Spokane, Wash. 99208

[21] Appl. No.: 645,229

[22] Filed: Aug. 29, 1984

[51] Int. Cl.$^4$ ............................................. A61B 5/08
[52] U.S. Cl. ..................................... 128/725; 272/99; 73/861.35
[58] Field of Search ................. 128/716, 725-730; 272/99; 73/861.35, 861.56, 861.64

[56] References Cited

U.S. PATENT DOCUMENTS

| | | | |
|---|---|---|---|
| 180,842 | 8/1876 | Burt | 128/729 |
| 1,044,367 | 11/1912 | Evans | 272/99 X |
| 4,158,360 | 6/1979 | Adams | 128/725 |
| 4,170,228 | 10/1979 | Elson et al. | 128/725 |
| 4,182,347 | 1/1980 | Russo | 128/725 |
| 4,220,162 | 9/1980 | Clark et al. | 128/719 X |
| 4,232,683 | 11/1980 | Bartholomew et al. | 128/725 |
| 4,259,951 | 4/1981 | Chernack et al. | 128/725 X |

Primary Examiner—Kyle L. Howell
Assistant Examiner—Angela D. Sykes
Attorney, Agent, or Firm—Keith S. Bergman

[57] ABSTRACT

A small, portable instrument to measure oral or nasal air flow during speech for both diagnostic and therapeutic purposes. The instrument provides a receptor at one end communicating by an elongate air passageway to a vertical measuring cylinder carrying a sphere vertically movable therein responsive to air flowing therethrough. The vertical position of the sphere in the measuring cylinder indicates amount of air flow and its change in vertical position indicates change in outflow through the receptor at any particular time. Parameters of the instrument may be varied to maintain measurements within the height limitation of the measuring cylinder, and the cylinder may be calibrated for absolute measuration.

4 Claims, 10 Drawing Figures

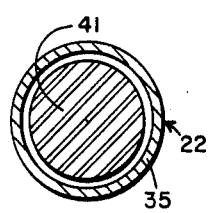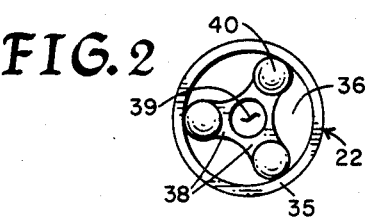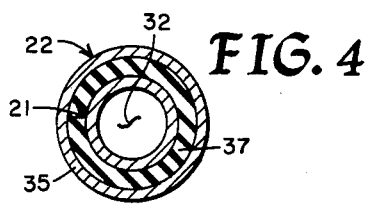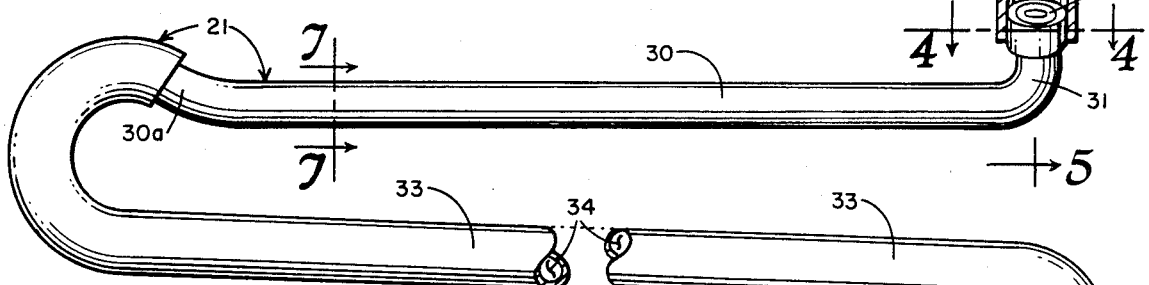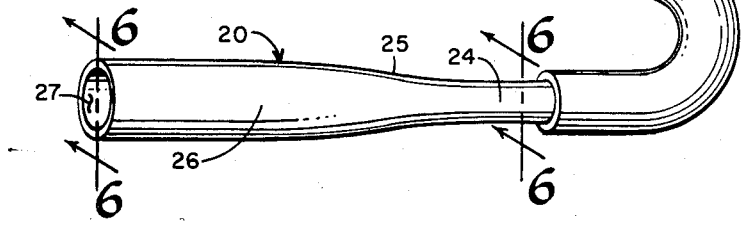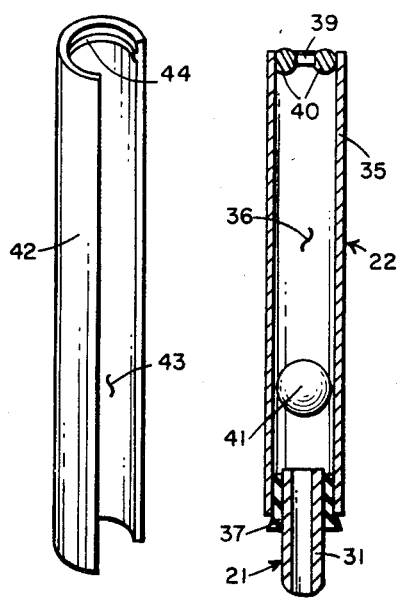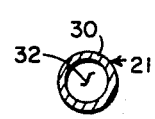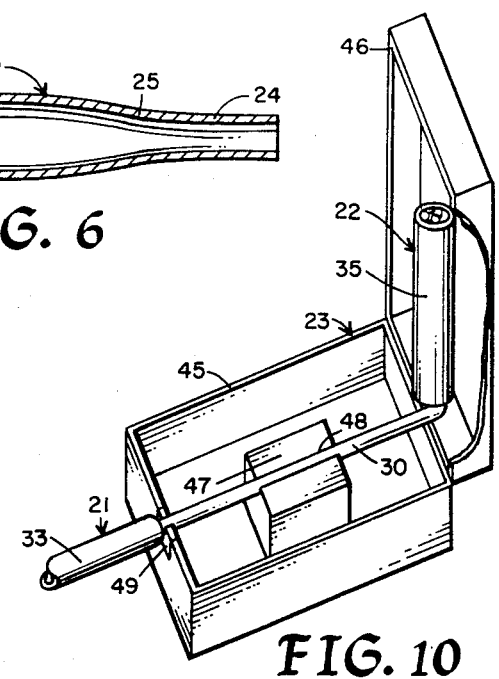

AIR FLOW MEASURING INSTRUMENT FOR SPEECH THERAPY

BACKGROUND OF INVENTION

Related Applications

There are no applications related hereto heretofore filed in this or any foreign country.

Field of Invention

My invention relates generally to measuring and testing instruments and more particularly to an air flow meter for use in speech therapy to measure air flow from nasal or oral cavities during speech.

Description of Prior Art

The production of speech is a complex interreaction of physical, physiological and psychological phenomena wherein a speaker's respiration moves a stream of air through the larynx, which impresses it with acoustic energy by a process known as phonation, and subsequently through the oral and nasal cavities where it is resonated and restructured by a process known as articulation to produce an aurally perceivable, comprehensible, energy that we call speech. The process is sufficiently complex that until the recent past, at least, it has been dealt with, understood and analyzed largely subjectively by its audio results rather than by means of any objective scientific measurement. The instant invention seeks to provide an instrument that objectively measures some forms of speech quality and particularly one which measures, either absolutely or comparatively, the flow of air from either nasal or oral passages for use principally in speech therapy, either as a diagnostic or remedial tool.

Most normal speech articulation is carried on in the oral cavities. Undoubtedly because of this, most attention in speech therapy has been directed toward various aberrations of these activities in the oral cavities rather than aberrations that may occur in the nasal cavities. Resonance in the nasal cavities, however, is a necessary part of certain elements in speech, particularly as in the case of the three semi-vowels of English /m/ as in 'mummy', /n/ as in 'nancy' and /n/ as in 'singer', all of which are produced with a complete occlusion of the oral cavity. Various similar aberrations of resonance and air passage in the nasal cavity, as in hypernasality, denasality, assimilated hypernasality and nasal air emission, must oftentimes be diagnosed and dealt with remedially in speech therapy. The problems associated with nasal resonance and air passage have probably been the most neglected areas of speech and language therapy and have generally presented a confusing area of semi-knowledge, as evidenced by the literature, brought about principally by subjective measurements and a lack of tools for objective measurement.

By far the bulk of nasal air flow and resonance problems have heretofore been analyzed and treated on the basis of subjective audio analysis of a speech and language by a therapist. This procedure, with its lack of objective standards in the measurement and testing, has produced a bewildering array of information which is about as varied as the subjective standards of the therapists involved. In the recent past some objective standards of measurement have been applied to nasal air emissions in therapy, centered principally about two measuration principles; the first, a liquid filled manometer, and the second, a mechanical pressure gauge. Neither of these methods of measurement have proven completely successful because each in essence measures a static pressure at a particular instant of time rather than a dynamic rate of air flow from the nasal cavity over an elapsed period and generally by reason of the manner in which the measurement is made, normal air flow from the nasal cavity must be stopped or at least substantially modified during the measurement per se and ordinarily for a period of time both before and after, all of which tends to effect resonance in the nasal cavity and thusly the articulation that is sought to be measured in the first instance. These known methods of measuration of nasal air pressure thusly have not proven too effective as they do not directly measure the condition sought to be determined, and change that condition by reason of the measurement.

Cineflurography and spectrographic analysis of voice samples have also been used somewhat in the recent past in analyzing and dealing with problems of nasal articulation. Both processes, however, are complex, relatively difficult and expensive and often not readily available to many speech therapists. Each process, again, is only indirectly related to problems of nasal resonance or air flow as each measures secondary characteristics of the acoustics or physiology related thereto. Neither process has proven satisfactory or been accepted in analyzing and treating problems of nasal articulation in speech therapy.

The instant invention seeks to provide a new clinical tool to continuously measure and indicate the existence, quality and quantity of air flow from the nasal cavities during normal speech activities without affecting those cavities during the process, to serve as both a diagnostic and remedial tool for a therapist. The instant invention is readily distinguishable from the pressure gauge type devices hereinbefore described in that it measures the existence, quality and quantity of the air flow from the nasal cavities rather than the pressure of that air within those cavities at a particular time. In so doing my device does not substantially affect the air flow from the nasal cavities and therefore does not affect the articulation processes therein as do the manometric type measuring devices. My invention is distinguished from the cineflurographic type devices in that the two devices measure different things, my device measuring air flow while the cineflurographic device measures anatomical position of various of the peripheral elements defining the nasal cavity. Similarly my device is distinguished from the voice spectrograpic analyzers in that they measure the acoustical quality and quantity of sounds produced from the whole vocal channel, including the articulation processes of both the oral and nasal cavities, which make it difficult, if even possible, to separately analyze the nature and quality of nasal articulation.

Secondarily my invention with an appropriate interchangeable oral receptor may also measure quantity and quality of air flow from the oral cavity, especially outwardly of the teeth and between the lips. The oral receptor is small enough to distinguish the lateral position of an emission from the oral cavity. It is therefore especially useful with lateral sibilant, fricative and affricative sound productions, aberrations and modifications.

My invention also provides a measuration tool that is portable, of relatively small size and of economic manufacture so that it may be readily available to therapists and others concerned with speech problems for general use in nonclinical surroundings, whereas this is not the case with the more sophisticated and costly devices of the prior art.

My invention thusly differs in both structure and function from known devices providing measurements relating to oral or nasal articulation either individually or collectively in that the known devices do not measure air flow and may change conditions of speech processes during measuration.

SUMMARY OF INVENTION

My invention generally provides a receptor communicating by an elongate air passageway to a vertical cylinder for measuring air flow therethrough. My receptor may be a curvilinear nasal bulb positionable in the nasal channel of a user or an oral funnel positionable between the lips of a user. The receptor is carried at one end of an air passageway, part of which is rigid and part of which may be flexible, that communicates from the receptor to a transparent, peripherally defined, vertical measuring cylinder. The cylinder carries a light weight sphere, slightly smaller than the internal diameter of the channel defined therein, so that the sphere may be raised in the cylinder responsive to the amount of air flowing through the cylinder and about the sphere. The measuring cylinder may be provided with graduations to aid measuration of sphere position therein. The uppermost portion of the cylinder is provided with a stop that permits the relatively free flow of air therethrough but prevents passage of the sphere. A cylindrical opaque shield is provided to fit about the measuring cylinder to prevent a patient's reviewing measuring sphere motion to aid diagnostic operations with the device. Receptor and measuring sphere parameters, especially size, may be varied to keep operative ranges within the physical limits of the device and provide maximum sensitivity.

An ancillary container is provided for the device with support means to positionally maintain and support it during use.

In creating such a device it is:

A principal object of my invention to provide a diagnostic and therapeutic instrument to measure air flow exiting from the speech channels during speech.

A further object of my invention to provide such an instrument that measures air flow associated with speech activities without disrupting that flow or modifying its normal operations to any substantial extent, especially as during speech.

A futher object of my invention to provide such an instrument that may be used to measure such air flow either from the nasal or the oral channels and to determine its lateral position in exiting from the oral channel.

A still further object of my invention to provide such an instrument that is of a small, compact nature such that it may be readily used as a portable hand manipulable device but yet may be supported on an ancillary container for stationary use as in clinical testing or therapy.

A still further object of my invention to provide such a measuring device that has a relatively short measuring cylinder and yet maintains measuration with in the limits of that cylinder by varying instrument parameters, especially density of the measuring sphere.

A still further object of my invention to provide such a device that has a removable shield that may be placed about the measuring cylinder to prevent patient observation and possible consequent reaction during diagnostic testing.

A still further object of my invention to provide such a device that is of new and novel design, of rugged and durable nature, of simple and economic manufacture and one otherwise well suited to the uses and purposes for which it is intended.

Other and further objects of my invention will appear from the following specification and accompanying drawings which form a part hereof. In carrying out the objects of my invention, however, it is to be understood that its essential features are susceptible to change in design and structural arrangement with only one preferred and practical embodiment being illustrated in the accompanying drawings as is required.

BRIEF DESCRIPTION OF DRAWINGS

In the accompanying drawings which form a part hereof and wherein like numbers of reference refer to similar parts throughout:

FIG. 1 is a partially cut-away, isometric view of my invention showing its various parts, their configuration and relationship.

FIG. 2 is a somewhat enlarged orthographic top or plan view of a tridactyl stop in the uppermost portion of the measuring cylinder.

FIG. 3 is a somewhat enlarged, horizontal, cross-sectional view through the measuring cylinder at the level of the measuring sphere, taken on the line 3—3 of FIG. 1, in the direction indicated by the arrows thereon.

FIG. 4 is a somewhat enlarged, horizontal, cross-sectional view through the interconnection of air channel with measuring cylinder, taken on the line 4—4 of FIG. 1, in the direction indicated by the arrows thereon.

FIG. 5 is a vertical, cross-sectional view of the measuring cylinder, taken on the line 5—5 of FIG. 1, in the direction indicated by the arrows thereon.

FIG. 6 is an elongate, vertical, cross-sectional view through an oral receptor, taken on the line 6—6 on FIG. 1, in the direction indicated by the arrows thereon.

FIG. 7 is a vertical, cross-sectional view through the rigid air channel element, taken on line 7—7 of FIG. 1, in the direction indicated by the arrows thereon.

FIG. 8 is an isometric view of a nasal receptor that may be carried by the end part of the air channel to communicate with a nasal channel of a user.

FIG. 9 is an isometric view of an opaque shield that may be used to partially cover the measuring cylinder to prevent patient view thereof during testing.

FIG. 10 is an isometric view of my measuring instrument supported for stationary use by an associated open container.

DESCRIPTION OF THE PREFERRED EMBODIMENT

My invention provides generally receptor 20 communicating by air passageway 21 with measuring cylinder 22 to measure air flow through the device which may be hand held or used in stationary fashion as when supported by container support 23.

Receptor 20, as shown particularly in FIG. 1, comprises a nasal funnel with smaller connecting tube 24 communicating by transition portion 25 to larger funnel portion 26, all of these elements constituting surfaces of revolution peripherally difining nasal funnel channel 27. The configuration and dimensioning of this element are not particularly critical except for the nasal funnel diameter which should be such as to conformably fit within the nasal orifice of a patient so that the external surface of the nasal funnel is immediately adjacent the internal surface defining a patient's nasal channel, immediately inwardly of its orifice, to prevent passage of any substantial air flow between the nasal funnel and the nasal channel walls. Because of the varying size of nasal channels in different patients, it is preferred that a plurality of variously sized nasal funnels be provided for use with my invention. Three funnels having external diameters of six, eight and ten millimeters respectively are sufficient for most normal use, especially when aided by the somewhat deformable nature of a patient's nasal channels.

The size of the smallest cross-sectional area of funnel channel 27, which normally occurs in connecting tip 24, may also affect the use of my device to some degree. This channel should be sufficiently large to prevent any substantial aerodynamic effects or create any back pressures on air passing therethrough from the nasal cavity. I have found that a channel of at least approximately one-quarter inch diameter is appropriate for this purpose in view of the quantity of moving air involved in normal nasal air flow. The funnel type nasal receptor, illustrated in FIGS. 1 and 6, is particularly adapted for use with an air passageway that is at least partially flexible as is the case when my measuring device be used in stationary mode. This type of nasal funnel also may be conveniently used to measure air flow from the oral channel, especially when carried between the lips and outwardly of the teeth of a patient.

A specie of receptor for use in a portable mode, with a totally rigid air passageway, is shown in FIG. 8. This receptor comprises nasal guard 28 of a relatively short length defined by a bulbously configured surface having a maximum diameter in the same general range as that of the funnel portion of the funnel type receptor, normally about eight to ten millimeters. The nasal guard defines medial cylindrical channel 29, for air passage, that again is preferably no smaller than the air passageway defined in connecting tube 24 of the funnel type receptor, normally at least approximately one-quarter inch. One end portion of this channel is sized to provide a frictionally maintainable fit upon the rigid elbow portion of air passageway 21. Again, if desired, a plurality of nasal guards of varying maximal diameters may be provided to fit variously normally sized nasal passageways of patients, but because of the peculiar external shape of this element a single guard ordinarily may be used through wider range of sizes of nasal passageways than can nasal funnels; and, oftentimes, one guard may be sufficient for most purposes depending especially upon its particular configuration and degree of insertion in a nasal channel.

Both the nasal guard and nasal funnel are formed from some reasonably rigid, durable material that may be sterilized by normal sterilization procedures existent in present day medical practices. Preferably the nasal funnel will be formed from glass or plastic and the nasal guard from a reasonably dense, nonporous rubber or plastic.

Air passageway 21 defines an enclosed elongate channel between nasal receptor 20 and measuring cylinder 22, as illustrated particularly in FIG. 1. This passageway includes a rigid, tubular elbow element having longer arm 30 and shorter arm 31 communicating in substantially perpendicular relationship. Each arm peripherally defines continuous air channel 32 extending therethrough. Preferably this element is formed from rigid, impervious tubular material such as glass or dense plastic. The outer end part 30a is bent (in a plane passing through the rigid elbow) slightly toward the shorter arm as illustrated. The configuration and dimensioning of the elements are not particularly critical except that channel 32 should have a cross-sectional area that is substantially the same as that of connecting tube 24 of the nasal receptor, that is, not less than approximately one-quarter inch in diameter. For convenience of operation shorter arm 31 is approximately one inch long and longer arm 30 is preferably approximately six inches long.

The flexible portion of air passageway 21 between funnel receptor and the rigid portion of that passageway comprises elongate resilient tube 33 defining medial air channel 34, again preferably of a cross-sectional area substantially the same as that of channel 32 of the rigid tube, when measured with the flexible tube in a relaxed position. Tube 33 is formed of some reasonably durable sterilizable material such as surgical rubber tubing. The tube should have sufficient elasticity and deformability to allow it to be interconnected to both connecting tube 24 of a nasal receptor and rigid elbow 30, 31 by overlapping as illustrated. Preferably, for convenience of operation, the flexible tubing will be approximately twenty four inches long and will have a substantially circular cross-section.

Measuring cylinder 22 provides open ended, rigid, circular cylinder 35 peripherally defining similarly shaped medial channel 36. The absolute dimensioning of this cylinder again is not particularly critical except as it relates to the relative dimensioning of the other elements of my invention. Preferably for convenience and to be in harmony with the other dimensions hereinbefore specified, the cylinder will be approximately three inches in length (in axial direction) and will define a channel having a diameter of approximately three-eighths of an inch. The cylinder is formed of a rigid, durable, sterilizable, material that is transparent, such as glass or dense plastic.

The lower orifice of cylinder 35 is provided with annular washer 37 to establish a substantially air tight, frictionally maintainable fit between the end portion of shorter arm 31 of the rigid elbow and the lower, internal portion of the measuring cylinder when the elements be positioned in an interconnecting relationship as illustrated in FIG. 1. This washer is formed of an elastically resilient material that is relatively impervious to air and provides some frictional competence between it and adjacent surfaces. Rubber or plastic polymers are suited to this purpose.

The upper portion of cylinder 35 carries a tridactyl stop having radially spaced interconnecting arms 38 defining air hole 39 in their medial interconnecting portions and bulbous protuberances 40 in their peripheral end parts to prevent a measuring sphere carried in cylinder 35 from stopping air hole 39. The stop has a peripheral diameter substantially the same as the internal diameter of channel 36 defined in measuring cylinder 35 so that it may be placed and thereafter positionally maintained by friction in the upper part of the measuring cylinder to prevent a measuring sphere from passing out of the upper portion of that cylinder. Again, the exact configuration of the tridactyl stop is not critical so long as it maintains the measuring sphere in the measuring cylinder, does not allow that sphere to be forced against the lower surface of the stop in a fashion to prevent free air flow upwardly through and out of the measuring cylinder and does not substantially affect air flow therepast. For best operation of my invention the combined or total cross-sectional area of openings in the stop should be at least substantially as great as the cross-sectional area of air passageway 21.

Measuring sphere 41 is carried within channel 36 of the measuring cylinder. This element is of spherical shape and a diameter somewhat less than that of channel 36 so that the sphere is free to move within that channel and leave a space between its periphery and that of the surface defining the channel. For a device formed with the preferred dimensions hereinbefore set forth, the difference between these diameters should be approximately six hundredths of an inch. The measuring sphere is formed of some fairly low density material such as expanded polystyrene to maintain its normal operating range within the dimensional limitations of measuring cylinder 35 and yet maintain appropriate accuracy when measuring normal nasal air flow. Preferably a plurality of measuring sphere will be provided for use with my invention, each sphere having the same physical size and shape but differing in mass, to assure maintenance of operational limits within the limitations established by the vertical height of the measuring tube, since in speech therapy there may be a substantial variance in air flow required to be measured, especially in dealing with some pathology problems.

If oftentimes is convenient or even necessary, especially during diagnostic procedures, to prevent a patient from seeing the results of nasal air flow measurement during testing operations to prevent either a voluntary or involuntary reaction to the test results. To accomplish this I provide opaque shield 42 formed as three-quarters of a peripherally defined cylinder, to define shield channel 43 which is of substantially the same size and shape as the external surface of measuring cylinder 35. The shield in its uppermost portion is provided with inwardly projecting boss 44 to positionally align the device on a cylinder being serviced. The shield is formed of opaque material of a semi-rigid elastically deformable nature so that it may be placed about cylinder 35 either by snapping it over the cylinder or by slipping it downwardly thereover and thereafter maintained by friction. The opening in the shield may be arranged by appropriate manual manipulation so that the measuring cylinder and the measuring sphere may be viewed by a therapist but not by a patient being dealt with.

In using my invention it is convenient, especially in clinical type surroundings, to have the measuring cylinder releasably positionable on some support. This may be accomplished, as illustrated in FIG. 10, by providing box 45 hingeably supporting lid 46 for maintenance in an open position to act as such a support. Retentively resilient support block 47, of appropriate dimension and configuration, extends upwardly from support in the medial part of the bottom of box 45 to define in its upper surface elbow channel 48 to releasably receive and support longer arm 30 of the elbow. A similar second retentively resilient support 49, in the form of an appropriately positioned insert, in the uppermost part of box 45 defines a channel in its uppermost surface to releasably receive the elbow at another point to provide two point support for it. Each channel supporting the elbow must releasably but securely support it and be appropriately positioned to maintain the measuring cylinder in a substantially vertical position once it be so placed.

Box 45 may be conveniently used as a container for the various elements of my invention and, if desired, may be appropriately furnished (not shown) to create cavities for containment and protection of each individual element of my invention, all as well known in the instrumentation arts.

Having thusly described the structure of my invention its operation may be understood.

Firstly, the various elements of my invention are formed according to the foregoing specification.

To assemble my instrument in a portable mode (not illustrated), measuring cylinder 22 is provided with tridactyl stop 38, 39 in the upper portion of cylinder 35, measuring sphere 41 within channel 36 and rigid elbow 30, 31 connected with the lower portion of the cylinder by annular washer 37 positioned therebetween. Nasal guard 28 is positioned on the outermost end part of the longer arm 30 to complete the assemblage. To use this my invention in this mode the instrument is manually manipulated to position the nasal guard in a nasal channel of a patient, somewhat inwardly of its orifice, with measuring cylinder 22 extending in a substantially vertical orientation. Speech is then originated by the patient and air flow through and from the nasal cavity will cause air to flow through receptor 20 and air passageway 21 and into measuring cylinder 22. The measuring cylinder, in its null position without any air flow therethrough, will have measuring sphere 41 in its lowermost position resting on the uppermost projection of shorter arm 31 of the rigid air passageway elbow by reason of gravity. As air flows through the air channel it will move upwardly over the measuring sphere to overcome some degree the force of gravity acting on it, to thusly move the sphere upwardly in the measuring cylinder. The air flow will continue on past the measuring sphere and through the upper portion of the measuring cylinder thereabove to exhaust through the orifices in the tridactyl stop. Since the measuring sphere is relatively small and of relatively low density, the force required to raise it against gravity bias is quite small and thusly the air flow required to cause this force is relatively low. The height that the measuring sphere raises within the measuring cylinder 22 will vary responsively to the amount of air flow through the cylinder and thusly will serve as a measure of that air flow.

The same portable mode assemblage of my invention without the nasal guard may be used to measure air flow from the oral cavity, especially immediately outwardly of the teeth.

The stationary mode of my invention, illustrated in FIG. 1, provides measuring cylinder 22 communicating with short arm 31 of the rigid air passageway elbow with the longer arm of that elbow communicating with flexible tube 33 which in turn communicates with connecting tube 24 of a nasal funnel type receptor. To use this form of my invention, the measuring cylinder is preferably releasably maintained on some supportive stationary object, such as on box 45 as illustrated in FIG. 10, and nasal funnel 26 is positioned in the nasal channel of a patient in a fashion similar to that used for the nasal guard. The device thereafter may be operated in the same fashion as with the portable mode. This mode may also measure air flow from the oral cavity by proper placement of the funnel receptor.

Measuring cylinder 35 may be graduated, if desired, to aid comparative measurements or to provide some absolute measure of air flow through the cylinder. If this be done, obviously, the graduation will depend upon the relative parameters of the various elements and because of this the graduation is most easily and reliably established by empirical means rather than by any theoretical consideration. The relationship of measuring sphere height to amount of air flow is not a lineal one and may be complicated by aerodynamic problems particulary at higher air flow rates. Since normally in most testing and therapeutic procedures relative air flow is more important of consideration than absolute measurement of air flow, cylinder graduation is not too important a problem, at least in the present state of the art. Individual anatomical and physiological variations within patients are usually so great as to make any absolute measure of speech related air flow relatively meaningless and because of this no standards have yet been developed in the field relating to the absolute values of air flow and their meaning. In general, however, the air flows involved are something on the order of twenty cubic centimeters per minute and the dimensioning and physical characteristics of my device should be such as to measure air flow in this range and probably at least one hundred percent above and below it. Apparatus having the dimensioning and characteristics specified as preferential will accomplish this, though undoubtedly apparatus having appropriately related parameters and different absolute measure will also do so.

The normal problems associated with nasal articulation involve a patient's veloparyngeal closure. This may be quite readily determined by the nature and quantity of nasal emission which is directly indicated by my measuring device. The device thusly serves as a direct diagnostic aid for hypernasality, hyponasality and denasality. The instrument may also serve as a therapeutic tool in the conditioned response type treatment of these deficiencies and has been effectively so used.

Nasal emission problems are caused by some incomplete veloparyngeal closure and therefore are readily diagnosed with my device in the same fashion as hypernasality. Assimilated hypernasality may be diagnosed by observation of change in measuring sphere position during articulation of sounds adjacent to the nasl sounds /m/, /n/, and /n/ and may be treated by the condition-response type treatment with the patient observing the same characteristics.

My device also may be used for measurement of air flow from the oral cavity where it is especially valuable for diagnosis and treatment of lateral production of sibilant, fricative and affricate sounds.

It is to be particularly noted that in using my invention in speech, substantially no changes of any consequential nature are made in the speech patterns themselves, particularly in the quality or quantity of air flow or resonance through or in the speech cavities or channels.

It is further to be noted that my instrument is directly, sequentially and substantially instantaneously responsive to changes or variations in air flow from a nasal channel to aid especially in diagnoses and treatment of problems relating to assimilated hypernasality and from an oral channel to deal with lateral sound production.

It is further to be noted that though my invention measures an air flow through only one nasal channel at a time, this air flow will normally be directly proportional to total air flow from the nasal cavity unless there be some anatomical abnormality which is readily determinable by gross inspection or measuring comparative air flow through both nasal channels.

The foregoing description of my invention is necessarily of a detailed nature so that a specific embodiment of it might be set forth as required but it is to be understood that various modifications of detail, rearrangement and multiplication of parts may be resorted to without departing from its spirit, essence or scope.

Having thusly described my invention, what I desire to protect by Letters Patent, and what I claim is:

1. An instrument to measure air flow from speech channels comprising, in combination:
   an elongate air passageway having a rigid portion configured as an elbow and defining a medial air channel, the said rigid elbow portion having a longer arm and a shorter arm substantially perpendicularly related, with the longer arm having an end portion bent slightly toward the shorter arm and releasably carrying a nasal receptor at its end portion and the shorter arm having an end portion,
   a vertically oriented transparent measuring cylinder having a bottom portion, the cylinder defining an elongate medial channel extending therethrough and carrying a measuring sphere for vertical motion therein, said cylinder having means of preventing exit of the measuring sphere therefrom without substantially interfering with passage of air therethrough, said sphere being movable upwardly against gravity bias responsive to air flow through the measuring cylinder, the end portion of the shorter arm sealably communicating with the bottom portion of the measuring cylinder.

2. The invention of claim 1 having an opaque, resiliently deformable shield, configured as part of a cylinder and defining a medial channel of shape similar to that of the exterior of the measuring cylinder, to fit about more than half but less than all of the vertical periphery of the measuring cylinder, said shield being releasably maintained thereon.

3. An air flow measuring instrument for use in diagnostic and remedial speech therapy comprising, in combination:
   a substantially vertically oriented elongate measuring cylinder having a bottom portion and further defining a medial channel carrying a measuring sphere movable upwardly therein responsive to air flow therethrough, said medial channel having means of preventing exit of the measuring sphere therefrom but yet allowing substantially free flow of air therethrough,
   an elongate passageway, having a rigid tubular portion configured as an elbow with a shorter arm interconnected with the bottom portion of the measuring cylinder and a longer arm extending substantially perpendicularly from the shorter arm, the longer arm having an end portion bent somewhat toward the shorter arm,
   a receptor comprising a bulbous nasal receptor having an orifice and being releasably carried by the end portion of the longer arm of the elbow, said receptor adapted to be releasably positionable in a human speech channel immediately inwardly of its orifice, said elongate passageway providing communication between said measuring cylinder and said receptor.

4. An air flow measuring instrument for use in diagnostic and remedial speech therapy comprising, in combination:
   a substantially vertically oriented, rigid, elongate measuring cylinder having a bottom and defining a medial channel carrying a measuring sphere movable upwardly therein responsive to air flow therethrough, said medial channel having means of preventing exit of the measuring sphere from the top thereof but yet allowing substantially free flow of air therethrough;

an elongate air passageway, communicating with said channel, defined by a rigid tubular elbow having a shorter arm interconnected with the bottom of the measuring cylinder and a longer arm, extending substantially perpendicularly from the shorter arm, interconnected with an elongate flexible tube having a free end and carrying a receptor at said free end, and a receptor having an orifice, said receptor adapted to be releasably positionable in a human speech channel, immediately inwardly of its orifice, the receptor comprising a funnel, of smaller cross-section than an oral speech cavity in which it is to be used, interconnected by a transition portion with the free end of the flexible tube.

* * * * *